United States Patent [19]

Ballard

[11] 4,443,072
[45] Apr. 17, 1984

[54] PURGED WINDOW APPARATUS UTILIZING HEATED PURGE GAS

[75] Inventor: Evan O. Ballard, Los Alamos, N. Mex.

[73] Assignee: The United States of America as represented by the United States Department of Energy, Washington, D.C.

[21] Appl. No.: 365,133

[22] Filed: Apr. 5, 1982

[51] Int. Cl.$^3$ ............................................. G02B 7/00
[52] U.S. Cl. ................................. 350/584; 356/318; 356/246
[58] Field of Search .................... 350/584, 418, 319

[56] References Cited

U.S. PATENT DOCUMENTS 3,696,230 10/1972 Friedrich ........................... 350/584
4,240,691 12/1980 Holmqvist et al. ................. 350/584

FOREIGN PATENT DOCUMENTS 1039955 8/1966 United Kingdom ............... 350/584

Primary Examiner—John K. Corbin
Assistant Examiner—Lynn Vandenburgh
Attorney, Agent, or Firm—Samuel M. Freund; Paul D. Gaetjens

[57] ABSTRACT

A purged window apparatus utilizing tangentially injected heated purge gases in the vicinity of electromagnetic radiation transmitting windows, and a tapered external mounting tube to accelerate these gases to provide a vortex flow on the window surface and a turbulent flow throughout the mounting tube. Use of this apparatus prevents backstreaming of gases under investigation which are flowing past the mouth of the mounting tube which would otherwise deposit on the windows. Lengthy spectroscopic investigations and analyses can thereby be performed without the necessity of interrupting the procedures in order to clean or replace contaminated windows.

5 Claims, 3 Drawing Figures

PURGED WINDOW APPARATUS UTILIZING HEATED PURGE GAS

This invention is the result of a contract with the Department of Energy (Contract No. W-7405-ENG-36).

BACKGROUND OF THE INVENTION

The present invention relates generally to spectroscopic interrogation of flowing gas samples without interruption of the flow, and more particularly to a purged window apparatus in which spectroscopically transparent, inert purge gases are introduced in such a manner that the window, through which probing electromagnetic radiation is inserted, and signal electromagnetic radiation is retrieved for the purpose of investigating the nature of the flowing gas, remains free of contamination by deposition or by chemical attack by substances in said flowing gas.

Monitoring of flowing systems such as coal gasifiers, for example, for contaminant gas species has become increasingly important in recent years with the continued emphasis being placed on alternative energy sources. Development of on-line, real-time gas species or particulate detection and analysis procedures has been problematic because of the destructive nature of the flowing gases. That is, mechanical or electrical probes placed in such streams are quickly destroyed by particulate caused erosion or by chemical attack by corrosive species present. Remote spectroscopic analysis has therefore emerged as a viable analytical tool for such systems. In particular, laser-induced fluorescence, coherent antistokes Raman spectroscopy, and laser-induced dielectric breakdown spectroscopy lend themselves well to such hostile environments. However, in the three above techniques laser radiation must be introduced into the flowing medium, and emitted or perhaps transmitted radiation extracted therefrom to provide diagnostic information concerning the gas composition. Moreover, other spectroscopic detection schemes might require electromagnetic radiation from sources other than lasers, so that some form of electromagnetic radiation transparent material must be present. The major difficulty with using such transparent materials is that they usually become opaque rather quickly from deposition of material in the flowing gas or from direct chemical attack, even if said transparent material is placed away from the gas flow itself; that is, offset from the area of substantial material transfer.

In the past, a common solution to this problem was to place the transmitting windows at the end of short tubes externally attached to the chamber containing the flowing gases and into which a flow of purging gas is applied over the window surface to reduce the backstreaming of the flowing gas of interest onto the windows by providing a buffer zone. However, even with a substantial flow limited only by the gas handling capability of the flow chamber, the windows deteriorate in time, reducing the sensitivity of the detection system and finally necessitating their cleaning or replacement.

The apparatus of the instant invention, through the use of tubes with longitudinally tapered interiors and a turbulent vortex flow over the window surface provides virtually complete protection from window contamination at very modest purge gas flow rates. The vortex flow is achieved by injecting the purging gas tangentially in the vicinity of the windows. This eliminates any regions of zero flow within the tubes into which flow gas can backstream. Moreover, the lower purge gas flow rates avoid dilution of the process gas under investigation, and unnecessary waste of purified gas.

SUMMARY OF THE INVENTION

An object of the apparatus of the instant invention is to enable remote spectroscopic interrogation of flowing gas systems without contamination of the electromagnetic radiation transmitting windows.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus of this invention may comprise one or more externally mounted cylindrical tubes with longitudinally tapered internal cross-section onto which is mounted electromagnetic radiation transparent windows and into which a purging gas is injected for providing a buffer region between the flowing gas to be investigated spectroscopically and the transparent windows. The tubes are attached to the chamber containing said flowing gas in such a manner that the smaller bore end faces the chamber and a vacuum tight seal is formed. The particular number and arrangement of these tubes is determined by the nature of the spectroscopic technique employed. The transparent window is placed at the larger bore end of the tube and a vacuum tight seal formed between the window material and the tube. A plurality of injection means enter the tubes in the vicinity of the windows tangentially to the inner bore. These provide a vortex flow of the purge gas across the window surface thereby preventing the formation of any stagnant gas pockets inside the tubes into which the chamber process gas can backstream. The injection pressure means is adjusted such that a positive pressure exists in the direction of the chamber so that the purge gas flows toward the chamber with a throughput which can be handled by the test chamber flow or pumping system. The longitudinal taper causes the purge gas to accelerate as it approaches the chamber, thereby increasing the velocity of the turbulent flow into the chamber with resultant effective omission of process gas into the window assemby. The purge gas is heated to prevent water condensation on the external window surface during operation and on the internal surface during startup. Preferrably, the longitudinal taper has a 10° to 15° included angle and the tubes are about 7.0 to 11.4 cm long to provide an adequate minimum bore diameter of 1.3 to 1.6 cm inch while maintaining a window aperture of approximately 2.54 to 3.8 cm inch diameter. The effectiveness of the apparatus of the instant invention is independent of purge gas flow rate over a substantial variation in this parameter which derives from the tube bore and pressure.

The advantage of the instant invention is that no window degradation was observed during extensive experimentation using an especially destructive gas flow whereas purged window designs according to existing art allowed window contamination despite high purge gas flow rates. It is therefore now possible to monitor flowing gas concentrations by spectroscopic means over extended periods of time without having to interrupt the gas flow to clean or change the electromagnetic radiation transmitting windows and without diluting this gas or expending huge quantities of purge gas. Further, the tapered longitudinal cross-section is amenable to high energy laser beam insertion for laser-induced dielectric breakdown studies since here the laser beam is focused into the test section and emitted light from the pinpoint breakdown diverges to a focusing lens placed in front of a detector.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION OF THE INVENTION

Reference will now be made in detail to the present preferred embodiment of the invention, an example of which is illustrated in the accompanying drawings. Development of window assemblies purged with heated nitrogen was undertaken to permit laser beam insertion into and signal retrieval from out of a chamber in which flowing gas to be spectroscopically investigated is located. In particular, a coal gasifier, providing an atmospheric pressure, 500° F. gas stream to the test chamber was used to test the apparatus of the instant invention. Such a gas stream comprises coal particles, oxygen, steam and methane. Detection of minority contaminant species from the coal such as sodium and potassium, for example, using laser-induced dielectric breakdown spectroscopy was the principle focus of the effort. After testing several purged window concepts, the apparatus of the instant invention evolved.

Figure 2:
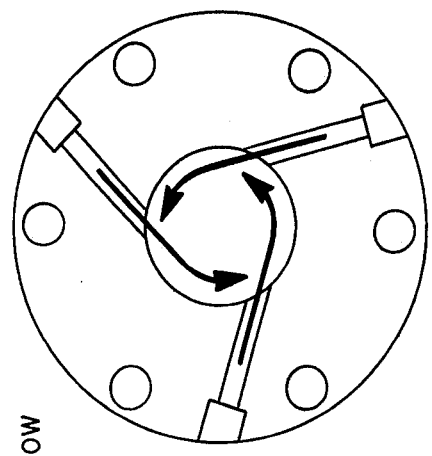
FIG. 2 shows the tangential arrangement of the purge gas injection means and the resulting vortex purge gas flow over the window surface.
Figure 1:
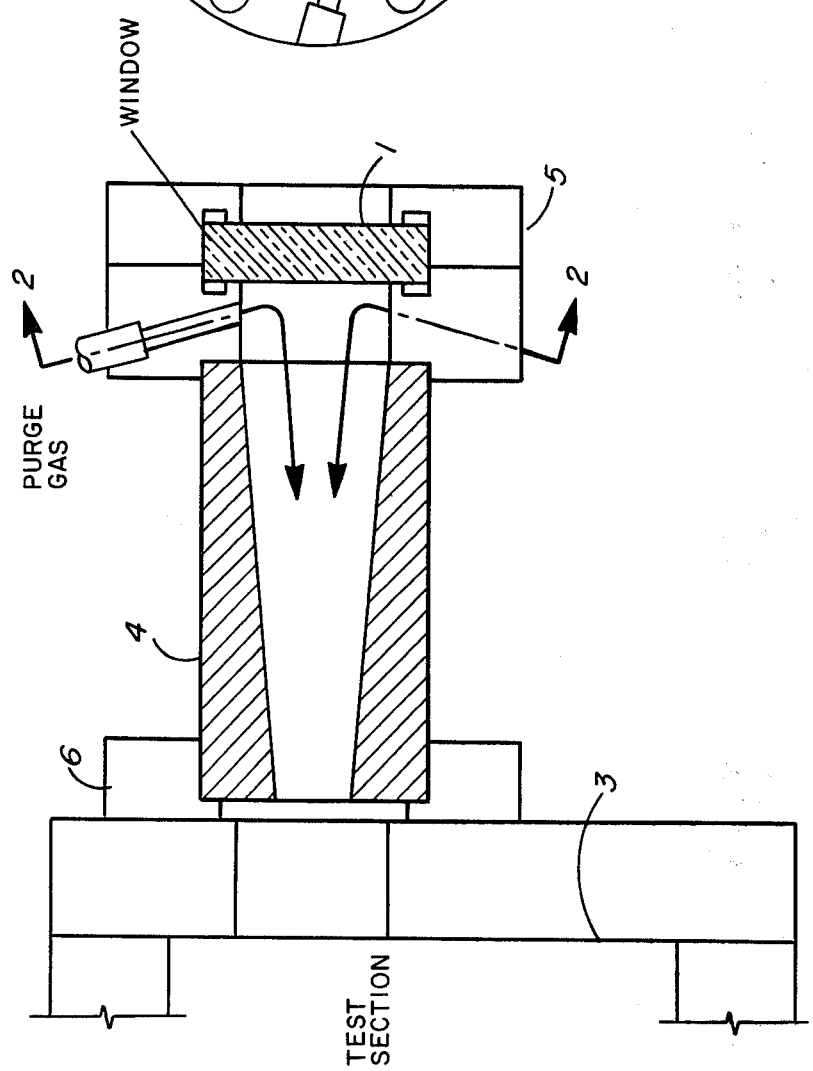
FIG. 1 is a schematic of the apparatus of the instant invention showing the placement of the window, the internally tapered tube, the test chamber, and the purge gas injection means.

FIGS. 1 and 2 are schematic views of the instant invention. In accordance with the invention, heated nitrogen purge gas was directed onto the inside surface of the transmitting window 1 by means of three symmetrically placed tubes 2 opening tangentially into the inner longitudinally tapered bore of a cylindrical transition section 4 at the end closest to the window. Nitrogen was supplied from commercially available gas cylinders fitted with gas regulators and heating tapes wound around the supply lines such that its pressure at the point of injection into the inner bore was 5–7 psi greater than the test chamber 3 pressure which was typically 2–3 psi above 1 atm, and its temperature was about 150° F. The nitrogen gas flowing at approximately 3.7 STD cu. ft./min. accelerates through the tapered transition section 4 toward the test chamber 3 due to the decreasing cross-sectional area in the direction of the flow, thereby providing an effective buffer zone between the gasifier product gas and the interior window surface. The combination of a vortex flow over the window surface, and the acceleration of the already turbulent purge gas flow prevented the recirculation of particulates and chemically active gases from the gasifier into the window assembly, thereby preventing ultimate contamination of the window surface. Even at 10–15 psi nitrogen pressures above the test section, the conventional single radial injection, non-tapered transition design resulted in contaminated windows within a few minutes of commencement of experiments. One transition section had dimensions of 7.0 cm for the length and an inner diameter decreasing from 2.5 cm at the window end to 1.8 cm at the test section end for an included angle of 10°. Another transition section was 11.4 cm long with diameters decreasing from 3.8 cm at the window to 1.6 cm at the test section for an included angle of 12°. The windows were removably attached to the transition section 4 by means of very standard flange and Viton o-ring assemblies 5. Similarly, the transition section was removably attached to the test section by a flange and copper gasket arrangement 6. Both attachments were rigid and vacuum tight.

Figure 3:
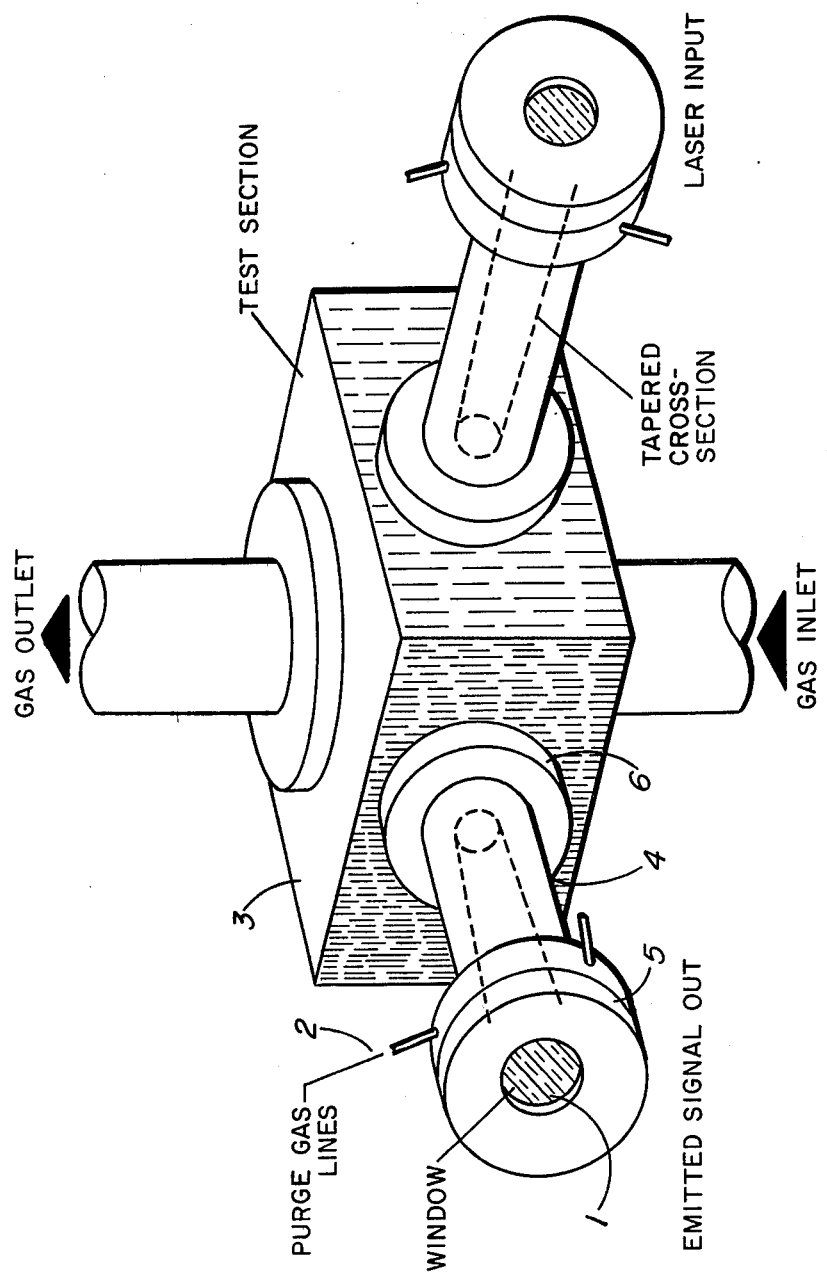
FIG. 3 shows an orthogonal deployment of the instant purged window apparatus useful for such spectroscopic diagnostics as laser-induced dielectric breakdown and laser-induced fluorescence, for example.

FIG. 3 shows the use of two of the purged window apparatus orthogonally disposed about a test chamber through which the gas under spectroscopic investigation flows. This configuration is suitable for laser-induced fluorescence and laser-induced dielectric breakdown spectroscopic investigations since as arranged, the laser light enters the flowing gas through one purged window, while the emitted fluorescence signals emerge at right angles through a second purged window apparatus.

Experiments using the conventional purging apparatus showed this design to be totally ineffective in preventing the particle-laden flow from depositing dust on the windows, thereby destroying the transmission of the laser beam. That is, a straight-bore cylindrical transition section with purge gas admitted radially in the vicinity of the windows did not work at any purge gas flow rate within the gas handling capabilities of the flow system. An intermediate design where a longer straight-bore transition section was used and the purge gas introduced tangentially provided a more effective buffer zone although some circulation of the flow stream into the region of the windows occurred with consequent deposition of contaminating material on the window surface. The apparatus of the instant invention, however, proved to be completely effective at maintaining clean windows during the coal gasifier operation. The heated nitrogen purge gas flow is accelerated as a result of the taper into the test section and provides a buffer zone without "dead flow" regions between the process gas stream and the windows thereby allowing lengthy spectroscopic investigations (many hours) to be performed without the necessity of interrupting the gas flow to clean or change the transmitting windows. As mentioned above, the tapered design of the instant invention is well-suited to laser beam insertion and retrieval of emitted signals since the laser beam is focussed into the test section and the emitted light radiates in a divergent fashion from the laser focus until it reaches a convergent focusing lens outside of the purged window apparatus.

To illustrate the apparatus of the instant invention, it was found that no degradation of window transmission occurred over a 1 hr. run time. Tests were terminated at this point because the desired information from the laser-induced dielectric breakdown spectroscopy had been obtained. Windows attached to either the conventional or intermediate design apparatus deteriorated within 20 to 40 min., with transmission substantially degrading early in the run. For example, after 20 min., light transmission was reduced to only 17% of its original value in a purged window apparatus of conventional design with 6-7 psi of nitrogen over the pressure in the test section maintained in the tube. It was found that increasing this pressure to 15 psi did not improve matters significantly.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A purged window apparatus for introducing probing electromagnetic radiation into and retrieving an emitted electromagnetic signal from out of a chamber of flowing gas upon which measurements are being made which enables long-term operation by reducing the necessity of interrupting the flow for the purpose of cleaning or replacing the radiation transmitting window material, said apparatus comprising:

(a) a plurality of tubes with cylindrical inner bore longitudinally tapered for accelerating purging gases with the smaller inner cross-section end directed toward the chamber and that of the larger inner cross-section directed away from the chamber whereon said tubes are externally disposed;
   (b) means for rigidly and removably mounting said smaller inner cross-section end of said tubes to the chamber, for providing a vacuum-tight seal, and for exposing said inner bore to the gas flow;
   (c) electromagnetic radiation transmitting material which passes with low absorption losses the probing and emitted electromagnetic radiation;
   (d) means for rigidly and removably mounting said radiation transmitting material onto said larger inner cross-section end and for providing a vacuum-tight seal;
   (e) injection means for introducing said purging gas tangentially to the inner surface of said cylindrical inner bore in the vicinity of said transmitting material and providing a vortex flow thereon and at such pressure that said purging gases flow and accelerate toward the chamber and into the chamber gas flow; and
   (f) means for heating said purging gas before it enters said injection means.

2. The apparatus according to claim 1, wherein said tubes have said longitudinally tapered bore having substantially 10°-15° included angle.

3. The apparatus according to claim 2, wherein said tubes are substantially 7.0 to 11.4 cm long and said larger inner cross-section is substantially 2.54 to 3.8 cm in diameter.

4. The apparatus according to claim 3, wherein said purging gas injection pressure is about 6 psi greater than the pressure inside the chamber of flowing gas.

5. The apparatus according to claim 4, wherein said purging gas is nitrogen heated to 150° F.

* * * * *